(12) United States Patent
Kerby et al.

(10) Patent No.: US 6,716,172 B1
(45) Date of Patent: Apr. 6, 2004

(54) MEDICAL DIAGNOSTIC ULTRASOUND IMAGING SYSTEM AND METHOD FOR DISPLAYING A PORTION OF AN ULTRASOUND IMAGE

(75) Inventors: Cynthia L. Kerby, Carnation, WA (US); Christian H. Marney, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 10/328,426

(22) Filed: Dec. 23, 2002

(51) Int. Cl.$^7$ ................................. A61B 8/00
(52) U.S. Cl. ....................................... 600/443
(58) Field of Search ................. 600/437–471; 73/599–633; 367/7, 11, 130, 138; 128/916

(56) References Cited

U.S. PATENT DOCUMENTS

| | | | |
|---|---|---|---|
| 5,345,938 A | * | 9/1994 | Nishiki et al. ............... 600/463 |
| 5,476,098 A | | 12/1995 | O'Donnell |
| 5,623,928 A | | 4/1997 | Wright et al. |
| 5,715,823 A | * | 2/1998 | Wood et al. ................. 600/437 |
| 5,924,986 A | | 7/1999 | Chandler et al. |

OTHER PUBLICATIONS

"Acuson Sequoia 512 Ultrasound System/Acuson Sequoia C256 Echocardiography System—User Manual," Acuson Corporation, pp. ii, 39–41, and 48–49 (1999).
"Acuson Cypress Echocardiography System—Operator's Manual," Acuson, A Siemens Company, pp. ii, 7–8, and 5–5 (2001).

* cited by examiner

Primary Examiner—Ali M. Imam (57) ABSTRACT

In one embodiment, a region of interest indictor is positioned over a first portion of an ultrasound image, and the first portion and at least some other portion of the ultrasound image are saved in a post-scan-converted format. The stored ultrasound image is played, and a region of interest indicator is positioned over a second portion of the played ultrasound image. In another embodiment, an ultrasound image is stored in a post-scan-converted format. The ultrasound image is played, and a region of interest indicator is positioned over a portion of the ultrasound image. In yet another embodiment, a user requests storage of a multi-frame ultrasound image for a first length of time. The ultrasound system instead stores the multi-frame ultrasound image for a second length of time, which is longer than the first length of time.

65 Claims, 4 Drawing Sheets

MEDICAL DIAGNOSTIC ULTRASOUND IMAGING SYSTEM AND METHOD FOR DISPLAYING A PORTION OF AN ULTRASOUND IMAGE

BACKGROUND

Some medical diagnostic ultrasound imaging systems allow a user to capture images for later playback and review. In particular, some ultrasound systems allow the user to capture a full-size, multi-frame ultrasound image (or "clip") for later playback and review. Some ultrasound systems allow a user to capture a quarter-size clip instead of the entire full-size clip. The user can play back the captured quarter-size clip in a quad-screen format to compare the captured quarter-size clip with other quarter-size clips. To capture a quarter-size clip, a user moves a quarter-size region of interest ("ROI") indicator (e.g., a highlighted box edge) over a displayed full-size image during image acquisition. Only the portion of the image bounded by the ROI indicator is captured, and only the captured portion of the full-size image can be played back during image review. If the user wishes to view a different portion of the image, the user must acquire another ultrasound image of the patient and repeat the above steps with the ROI indicator in the desired position.

The Cypress Echocardiography System by Acuson, a Siemens Company, offers a feature that reduces the need to re-acquire an ultrasound image. In the Cypress system, a user can store a full-size image clip in a temporary scrolling memory. If the user is not satisfied with where he positioned the quarter-size ROI indicator during image acquisition, the user can play back the full-size image clip from the temporary scrolling memory and reposition the ROI indicator. The full-size image clip can be transferred from the temporary scrolling memory to a magneto-optical disc and later loaded from the magneto-optical disc onto the same or different Cypress system to allow a user to later reposition the ROI indicator and capture a different quarter-size clip. However, because the full-size image clip is stored in the temporary scrolling memory and in the magneto-optical disc in a proprietary, hardware-dependent, pre-scan-converted format, the ability to reposition the ROI indicator can only be performed by systems that read that format.

SUMMARY

The present invention is defined by the following claims, and nothing in this section should be taken as a limitation on those claims.

By way of introduction, the embodiments described below provide a medical diagnostic ultrasound imaging system and method for displaying a portion of an ultrasound image. In one embodiment, a region of interest indictor is positioned over a first portion of an ultrasound image, and the first portion and at least some other portion of the ultrasound image are saved in a post-scan-converted format. The stored ultrasound image is played, and a region of interest indicator is positioned over a second portion of the played ultrasound image. The second portion is then played. In another embodiment, an ultrasound image is stored in a post-scan-converted format. The ultrasound image is played, and a region of interest indicator is positioned over a portion of the ultrasound image. The portion is then played. In yet another embodiment, a user requests storage of a multi-frame ultrasound image for a first length of time. The ultrasound system instead stores the multi-frame ultrasound image for a second length of time, which is longer than the first length of time. The same or different user can later request to play the multi-frame ultrasound image for a time other than that originally requested. Other embodiments are provided, and each of the embodiments described herein can be used alone or in combination with one another.

The embodiments will now be described with reference to the attached drawings.

DETAILED DESCRIPTION OF THE PRESENTLY PREFERRED EMBODIMENTS

Figure 1:
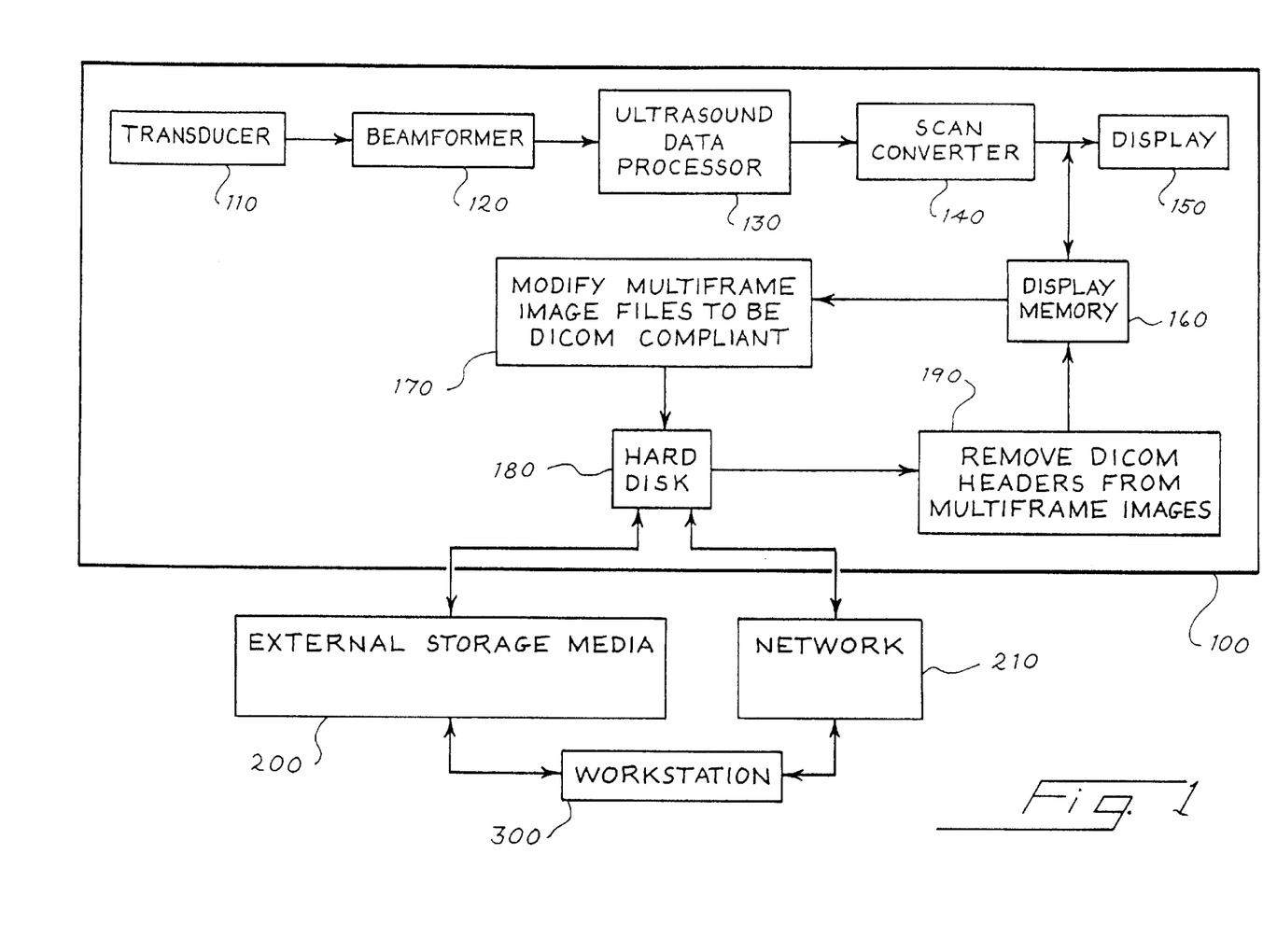
FIG. 1 is a block diagram of a medical imaging environment of a preferred embodiment.

Turning now to the drawings, FIG. 1 is a block diagram of a medical imaging environment of a preferred embodiment. The imaging environment comprises a medical diagnostic ultrasound imaging system 100 in communication with a workstation 300 via removable storage media 200 (e.g., a magneto-optical disk, a CD-ROM, a memory stick, etc.) and/or a network 210 (e.g., the Internet, a hospital or clinic intranet, etc.). The ultrasound system 100 and workstation 300 can communicate in other ways not shown in FIG. 1 (e.g., though a wireless communication device). In this environment, ultrasound images and other information can be saved in digital form in the ultrasound system 100 for later review or post-processing on the ultrasound system 100 or on the workstation 300. The workstation 300 is a computer comprising a display device, a user interface, and a processor that runs image review software that allows a user to retrieve and review a stored digital image and perform measurements and other post-processing activities on the image. Preferably, the external storage media 200 operates under a DICOM exchange media format, and the network 210 is DICOM compliant. Although the DICOM format is preferred because it is a standard for medical workstations, other formats and viewers (such as AVI) can be used.

The ultrasound system 100 comprises a transducer 110, a beam former 120, an ultrasound data processor 130, a scan converter 140, a display device 150, a display memory 160, a DICOM-header adder 170, a hard disk 180, and a DICOM-header remover 190. The ultrasound system 100 can comprise additional components, which are not shown in FIG. 1 to simplify the drawing. During an ultrasound examination, a sonographer contacts the transducer 110 with a patient. The beam former 120 controls transmit and receive hardware and applies a voltage to the transducer 110 to cause it to vibrate and emit an ultrasonic beam into the portion of the patient's body in contact with the transducer 110. Ultrasonic energy reflected from the patient's body impinges on the transducer 110, and the resulting voltages created by the transducer 110 are received by the beam former 120. The ultrasound data processor 130, which can take the form of one or more general processors, digital signal processors, application specific integrated circuits, logic devices, analog devices, or other electrical components, performs filtering, signal processing, and other functions used to generate an ultrasound image. The exact function of the ultrasound data processor 130 can vary depending on what imaging mode is used (e.g., B mode, BC mode, Dp mode, M mode, etc.). The ultrasound data processor 130 outputs ultrasound data to the scan converter 140. At this point, the ultrasound data is in a proprietary, hardware-dependent format. The scan converter 140 transforms the data from the proprietary, hardware-dependent format into a standard pixel data format (e.g., JPEG, RGB, YcbCr) so that an ultrasound image can be displayed on the display device 150. For example, the scan converter 140 can convert the ultrasound data from a polar coordinate format to a Cartesian coordinate format.

In addition to being displayed on the display device 150, a post-scan converted ultrasound image can be stored in the ultrasound system 100 and exported to the workstation 300. As used herein, the term "ultrasound image" refers to either a single image frame or a plurality of image frames, which may also be referred to herein as a "multi-frame ultrasound image" or an "image clip." In the embodiment discussed herein, the ultrasound image comprises a plurality of frames. To save an ultrasound image, the same type of data that would be sent to the display device 150 (i.e., an ultrasound image in a post-scan converted format) is stored in the display memory 160. The post-scan converted image data stored in the display memory 160 is made DICOM compliant by the DICOM-header adder 170. The DICOM-header adder 170, which can be implemented with hardware or with software running on a processor of the ultrasound system 100, modifies the multi-frame image files received from the display memory 160 to make them DICOM compliant. In one embodiment, the multi-frame ultrasound image comprises a plurality of image frames in JPEG format with a multi-frame (or clip) header. To make the multi-frame image DICOM compliant, a DICOM header is added in front of each JPEG image frame. The following is an example of a DICOM-compliant multi-frame image format:

Multi-frame image header
DICOM header
JPEG image frame
DICOM header
JPEG image frame
DICOM header
JPEG image frame
Etc.

The post-scan converted, DICOM-compliant ultrasound image is then stored in the ultrasound system's hard disk 180. Preferably, the storage capacity of the hard disk 180 is greater than the storage capacity of the temporary scrolling memory of the Cypress Echocardiography System by Acuson, a Siemens Company. The ultrasound image stored in the hard disk 180 can be stored in a file that is associated with a patient, and data for that patient can be made available for display until the data is erased from the hard disk 180. To play back the post-scan converted, DICOM-compliant ultrasound image from the hard disk 180, the DICOM-header remover 190, which can also be implemented with hardware or with software running on a processor of the ultrasound system 100, removes the DICOM headers in front of each JPEG image frame. The ultrasound image is then stored in the display memory 160 and displayed on the display device 150. As noted above, because the ultrasound image is stored in a post-scan-converted, standard pixel data format, the ultrasound image can be sent directly to the display device 150 from the display memory 160 without first being scan converted. The ultrasound image stored in the hard disk 180 can also be transferred to the workstation 300 via external storage media 200 or the network 210. By storing the ultrasound image in a post-scan-converted, standard pixel data format, the saved image can be viewed on any hardware. Further, images can be loaded onto ultrasound system's hard disk 180 from the workstation 300 to be displayed on the ultrasound system's display device 150.

Although the ultrasound image can be played back as a full-size image, it is often desired to only display a portion of the image. For example, in a stress echo exam, it is often desired to display ultrasound images in a quad-screen format, with each quadrant displaying a quarter-size portion of a different ultrasound image. During a stress echo exam, two sets of four ultrasound images (a parasternal long axis view, a parastemal short axis view, an apical four chamber view, and an apical two chamber view) are taken—one set while the patient is at rest and the other set during or immediately after stress (i.e., exercise or the administration of pharmacologic agents to increase the heart rate of the patient). The eight images are displayed side-by-side on two quad screens, allowing a physician to compare the rest and post-stress images of each view.

In several conventional ultrasound systems, to select the portion of the image for display in a quad-screen format, a sonographer positions a quarter-size region of interest ("ROI") indicator (e.g., a highlighted box edge) over a portion of a full-size ultrasound image displayed on the display device during image acquisition. After the sonographer positions the ROI indicator, the sonographer presses a button on the ultrasound system's user interface, and only the portion of the ultrasound image bounded by the ROI indicator is stored in the hard disk. The captured quarter-size portion is later displayed in one quadrant of a quad-screen display. A problem arises if a user who later reviews the images determines that one or more of the quarter-size images does not show the correct anatomy (i.e., that the ROI indicator was positioned over the wrong portion of the ultrasound image). In this situation, a new ultrasound image would need to be acquired with the ROI indicator positioned over the correct portion of the ultrasound image. This corrective action is often inconvenient because it requires a new examination of the patient.

This preferred embodiment overcomes the problem described above by allowing the playback of a captured portion of an ultrasound image to be dynamically changed post-acquisition. In this preferred embodiment, instead of merely saving the portion of the image bounded by the ROI indictor, the system 100 saves the bounded portion plus at least some other portion of the ultrasound image. For example, the system 100 can save the entire, full-frame image. Because more than just the bounded portion is saved, a reviewing user can later position a ROI indictor over a different portion of the ultrasound image instead of acquiring a new set of images if the ROI indicator was positioned in the wrong location during image acquisition. This preferred embodiment will now be illustrated in conjunction with FIGS. 2–5.

Figure 2:
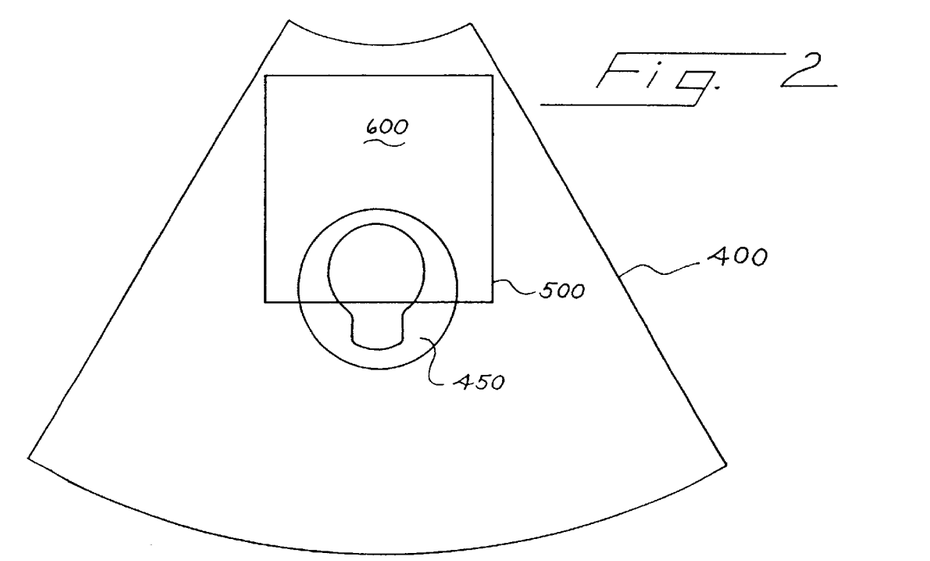
FIG. 2 is an illustration of an ultrasound image of a preferred embodiment with a region of interest indicator positioned over a first portion of the image.

FIG. 2 is an illustration of an ultrasound image 400 displayed on the display device 150 of the ultrasound system 100. The ultrasound image 400 shows a heart 450 under evaluation. When the sonographer is acquiring the ultrasound image 400, he positions a ROI indicator 500 over a first portion 600 of the ultrasound image 400 and presses an image capture button on the ultrasound system's user interface. In this embodiment, the system 100 saves the entire, full-screen image in a post-scan-converted format to the hard disk 180. Accordingly, not only is the first portion 600 of the ultrasound image 400 saved (as in prior systems), but the other portions surrounding the first portion 600 are also saved to the hard disk 180.

Figure 3:
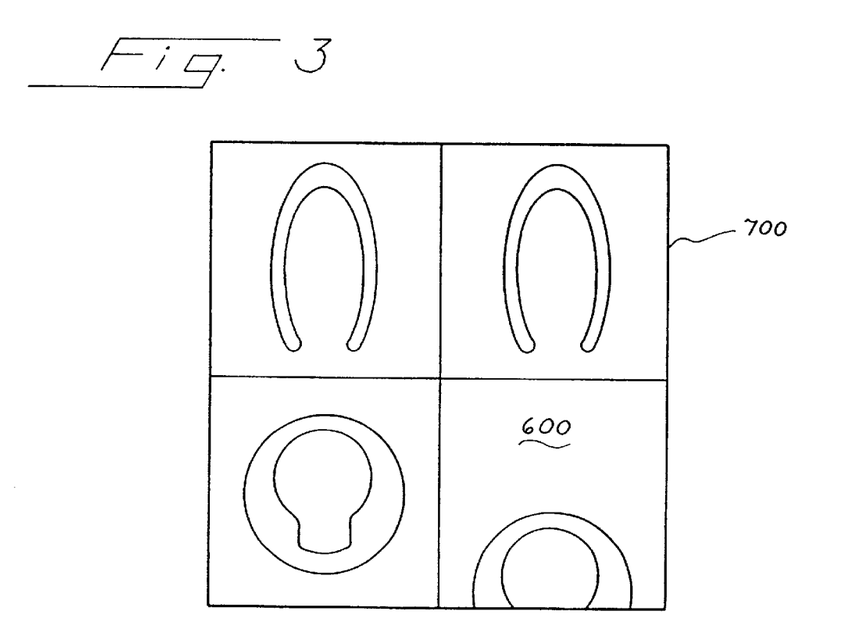
FIG. 3 is an illustration of a quad-screen display of a preferred embodiment displaying the first portion of the ultrasound image.
Figure 4:
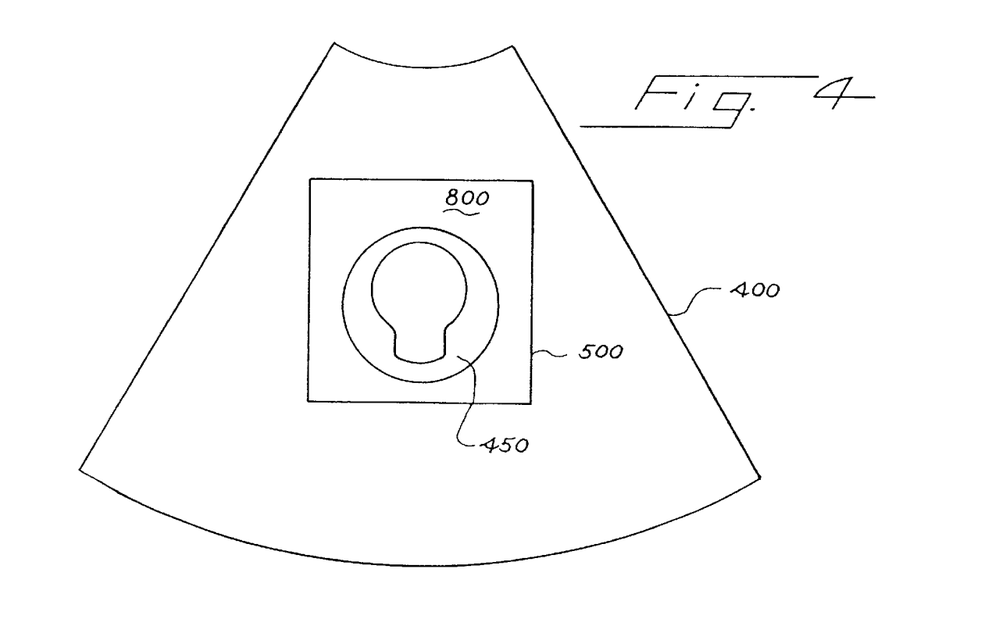
FIG. 4 is an illustration of an ultrasound image of a preferred embodiment with a region of interest indicator positioned over a second portion of the image.
Figure 5:
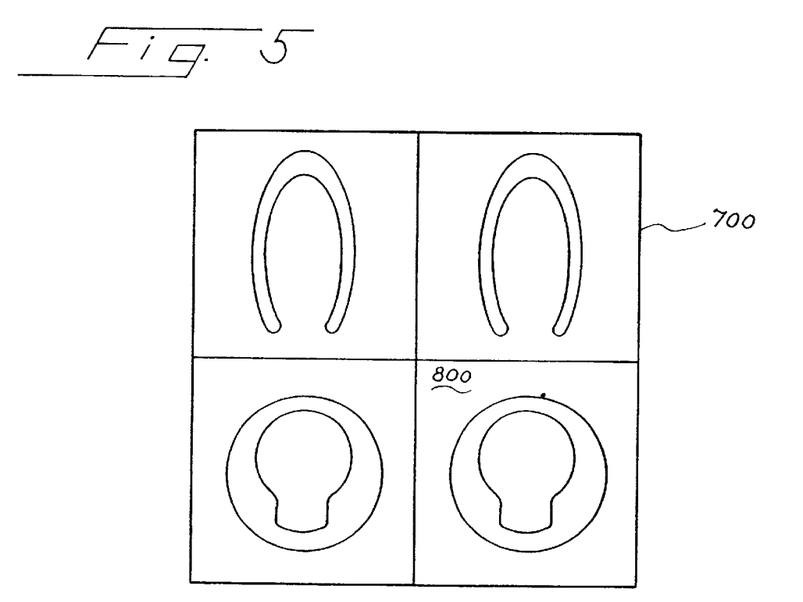
FIG. 5 is an illustration of a quad-screen display of a preferred embodiment displaying the second portion of the ultrasound image.

When the stored image is later reviewed by a reviewing user, only the first portion 600 is displayed. (The sonographer and the "reviewing user" can be the same person, such as when the sonographer plays the stored version of the ultrasound image from the hard disk 180, or can be a different person, such as when a physician reviews the stored version of the ultrasound image at the workstation 300.) As shown in FIG. 3, in this example, the saved first portion 600 is displayed in a quad-screen display 700 with three other quarter-size images. Here, the captured first portion 600 is not adequate for comparison purposes because the ROI indicator 500 was set to high on the ultrasound image 400 during image acquisition. With this preferred embodiment, instead of acquiring a new set of ultrasound images, the reviewing user simply plays back the stored full-screen image 400, and, at anytime during playback of the image 400, the user can reposition the ROI indicator 500 over the appropriate portion of the ultrasound image 400. As shown in FIG. 4, the user can reposition the ROI indicator 500 over a second portion 800 showing the appropriate part of the heart 450, and, as shown in FIG. 5, the quadrant of the quad-screen display 700 that formerly displayed the first portion 600 changes to display the second portion 800. In this way, the inadequate first portion 600 is replaced by the second portion 800 without requiring a new set of ultrasound images to be acquired.

There are several alternatives that can be used with these embodiments. For example, in the embodiment described above, the ultrasound system 100 captured the full-screen image and only played the portion of the full-screen image that was indicated by the ROI indictor during acquisition. In that embodiment, the sonographer positioned the ROI indicator over the ultrasound image during image acquisition to set a "default" portion that was displayed in a quad-screen format. Having the sonographer set such a default portion may be preferred because it eliminates the need for the reviewing user to view the full-screen ultrasound image and set the ROI indicator. Accordingly, the reviewing user would only need to position a ROI indicator if he decided that the portion selected by the sonographer was inadequate and wanted to modify the displayed portion of the multi-frame ultrasound image. (This also provides the advantage of reducing processing time. Multi-frame ultrasound images are sometimes compressed for storage and decompressed for playback. By setting the ROI indicator during image acquisition, only the default portion is decompressed for playback, and additional processing time for decompressing the remainder of the stored image is only necessary if the user wishes to reposition the ROI indicator.) However, because a ROI indicator can be positioned on a captured image during image review, a sonographer need not position a ROI indicator during image acquisition. Instead, in an alternate embodiment, the ROI indicator is set for the first time during image review. Eliminating the need for the sonographer to set a ROI indicator can simplify the sonographer's task and allow him to concentrate on acquiring a good image.

In another alternate embodiment, the ROI indicator used during image review is different from the ROI indicator used during image acquisition. In FIGS. 2–5, a reviewing user repositioned the same ROI indicator 500 that was set during image acquisition. That is, when the reviewing user played back the saved, full-screen ultrasound image, the ROI indicator 500 set by the sonographer was also displayed, and the reviewing user moved that ROI indicator 500 from the first portion 600 to the second portion 800. In an alternate embodiment, when the reviewing user plays back the saved, full-screen ultrasound image, the reviewing user positions a new ROI indicator over the second portion 800. The sonographer's original ROI indicator can be displayed (e.g., in the same or different color) for reference, or the new ROI indicator can be the only ROI indicator displayed.

In the embodiment described above, the stored version of the ultrasound image was a multi-frame image, and all of the frames were played back to the reviewing user as he positioned the ROI indictor over the second portion 800. In an alternate embodiment, when the stored version of the ultrasound image is played, only a single frame of multi-frame image is displayed, and the reviewing user positions the ROI indictor over the second portion on the single frame. In another alternate embodiment, more than one but less than all of the frames of the multi-frame image are played back when the reviewing user positions the ROI indictor over the second portion.

In yet another alternate embodiment, the stored version of the ultrasound image is more than just the first portion but less than the entire, full-frame image. For example, the stored image can be the first portion plus some portion directly surrounding the first portion (e.g., the stored image can be the first portion plus two centimeters of image surrounding the first portion on all sides of the ROI indicator). As another example, if the top part of the image does not contain any useful information (e.g., because of clutter), the top part of the image can be omitted from the stored version of the image. As yet another example, all of the frames within the first portion can be saved, while only some frames (e.g., every other frame) can be stored of the surrounding image. Each of these alternatives reduces that amount of storage space needed to store the image.

It should be noted that while the portion bounded by the ROI indicator in the above illustrations was ¼ the size of a full-frame image, a "portion" can be some other fraction of the image. Further, while the ROI indictor was shown to be a square, any size or shape (regular or arbitrary) can be used. Additionally, the portion of the image bound by the ROI indicator does not need to be displayed in a quad-screen format or used with a stress echo exam. The played-back portion can be any size (i.e., the same size as, smaller than, or larger than the portion of the image bound by the ROI indicator) and can be displayed in any display format (e.g., 4 up, 2 up, 6 up, etc). Also, the portion of the ultrasound image and the larger stored image (e.g., the full-frame image) can be played back at the same time (e.g., both played back on the same screen) or at different times (e.g., the display of one is toggled with the display of the other).

It should also be noted that while the preferred embodiments described above related to moving a region of interest indicator, the preferred embodiments can more broadly be characterized as modifying saved data by storing more than the requested data. The data stored has more information content than is contained in the image or images requested to be stored. The additional information content may be spatial or temporal image data and can exceed the request in extent or resolution or it can be non-image data from which additional information can be extracted. The following paragraphs provide examples of this general idea of storing more data than that requested so that the saved data can be later modified.

In one alternate embodiment, the stored version of an ultrasound clip is more than just first to last images in the clip that were requested to be stored. For example, the stored image can include image frames previous to the first frame requested stored and/or successive to the last frame requested stored. On review, the user can increase the temporal window over which the data is reviewed. In this way, the ultrasound system saves more temporal data than was requested by a user. In general, a user requests storage of a multi-frame ultrasound image for a first length of time. The ultrasound system instead stores the multi-frame ultrasound image for a second length of time, which is longer than the first length of time (e.g., the starting point is before the designated starting point and/or the ending point is after the designated ending point). The multi-frame ultrasound image can be stored in any desired format (e.g., pre-detected, RF data; pre-scan converted; or post-scan converted). The same or different user can later request to play the multi-frame ultrasound image for a time other than that originally requested. This embodiment finds particular use when a sequence of images in a cardiac cycle is captured. Data can be stored so that, on replay, the start frame can be moved earlier, the end frame can be moved later, or the frame rate can be increased. (In another embodiment, an image is stored and, on replay, the processing has changed to emphasize one or more regions or features in the image.) This application of capturing a multi-frame ultrasound image based on a patient's heart cycle will now be discussed.

Figure 6:
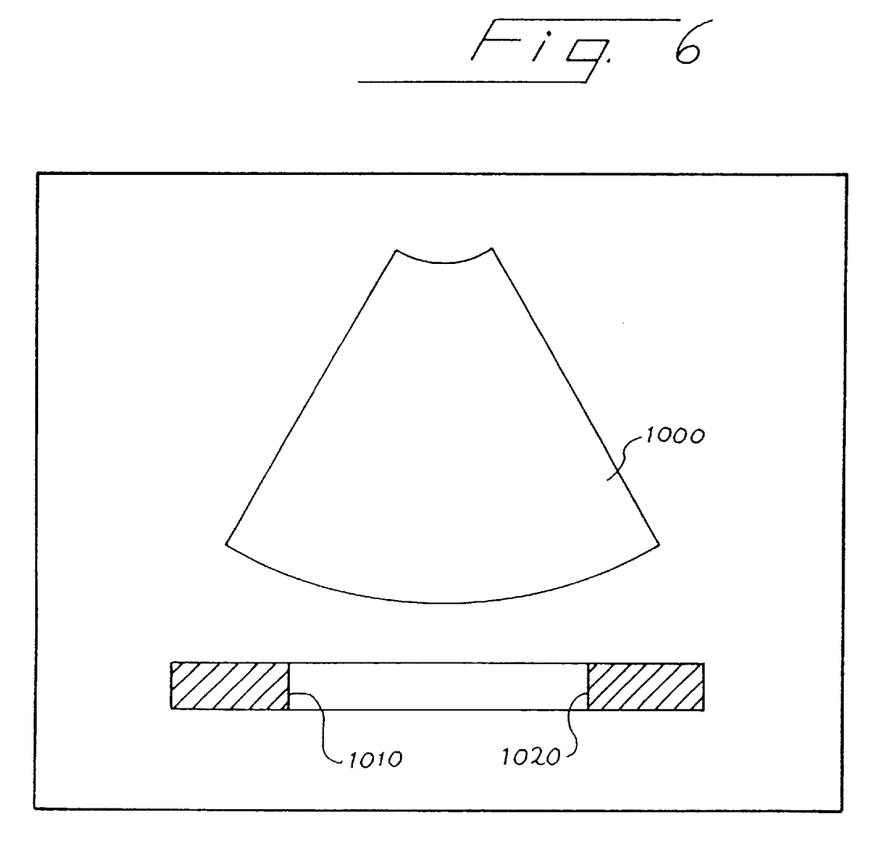
FIG. 6 is an illustration of an ultrasound image of a preferred embodiment.

Several existing ultrasound systems allow a user to define how much of a patient's heart cycle (r-wave to r-wave interval) to capture into a multi-frame image. Common practice is to only allow capture of the systole portion of the patient's heart cycle. Studies show that sometimes it can be useful to view the entire heart cycle or to view more than one entire heart cycle. This alternate embodiment allows the user to view more multi-frame image frames than he requested the system to capture. For example, if the user defines a preset to capture only the systole portion of the patient's heart cycle, the ultrasound system can capture the patient's full heart cycle. With reference to FIG. 6, when the captured multi-frame image 1000 is played for user review, the multi-frame image 1000 will display a visual indicator having left and right margins 1010, 1020. The margins 1010, 1020 are preferably placed such that only the systole portion of the patient's heart cycle will be played (i.e., the margins. 1010, 1020 are placed per the preset-defined portion of the patient's heart cycle that the user wanted to capture). This provides a display that the user may be accustomed to. The user can move either or both of the margins 1010, 1020 to view the captured image frames of the patient's heart cycle before and/or after the systole portion of the patient's heart cycle. Accordingly, with these margins 1010, 1020, a user can "margin off" collected data to view multi-frame image frames on either side of a preset defined amount of a patient' heart cycle. This allows a user to "peel open" a heart cycle in a captured multi-frame image to view more image frames of a heart cycle than originally requested (e.g., more than just the systole portion of patient' heart cycle).

Additionally, the ultrasound system can store and transfer the portion of the patient's heart cycle that the user wanted stored via the user setting the margins of the captured multi-frame image to indicate the portion that the system should store. This function can be used such that the user can define any portion of the heart cycle or the whole heart cycle or even more than one heart cycle he wants the system to capture, and the user can use the multi-frame margins to view any portion, more or less of the heart cycle, that he is interested in viewing during review of the captured multi-frame image.

In some of the embodiments described above, the ultrasound image was stored in a post-scan-converted format. In an alternate embodiment, the ultrasound image is stored in a pre-detected, element, beamformed (RF), or baseband (I/Q) data format. Using these formats allows additional modifications to be made to stored data. Before turning to these modifications, a general overview relating to these formats is provided.

Ultrasound imaging systems generally use transducer elements to generate and receive acoustic waves. The analog receive signal is transmitted to the transducer interface, which converts the analog signal to a digital signal on an element-by-element basis. Each transducer element can have its own channel and analog-to-digital converter. The beam former 120 imposes time delays and/or phase rotation to bring ultrasound pulses from different transducer elements into focus. Further processing generally assumes a center frequency for optimal processing. (This may be the center frequency of the transmitted waveform, a harmonic of that frequency, or any other frequency deemed optimal for the mode processor which follows.) Using this processing frequency, a base band processor shifts the RF data output by the beam former 120 to a base band frequency (the ultrasound data processor 130 can comprise a baseband processor and a mode (e.g., echo, flow) processor). The baseband processor can also be a useful place to remove data that will not be used in later processing. The data can be decimated to the resolution needed for creating the final display, and the start and end vector data used in creating the display can be limited. The baseband processor is not needed for all mode processors. Some processing, such as some methods of echo processing and elasticity imaging, do not need the data to be in baseband at all but may find the data reduction convenient. Baseband data can be thought of as having Inphase and Quadrature components and is often referred to as I/Q data. Mode processors process the data according to best means for extracting the information they seek. Common forms of mode processors are echo, flow, Doppler, M-mode, 3D, and harmonic imaging. Other, less common modes are elasticity imaging, acoustic streaming, and acoustic radiation force imaging. Some of these processors preferably use data pre-aligned on a predetermined grid, such as 3D, and some can be combined, as echo harmonic imaging. At some point along the processing chain, the data is converted to the display grid format. This is scan conversion.

With reference to FIG. 1, the ultrasound data processor 130 can be considered to contain a baseband demodulation component and a detector component. Accordingly, the input to the ultrasound data processor 130 is pre-detected, RF data, and the output is pre-scan converted data (i.e., post-detected, r-theta data). Instead of implementing these embodiments with post-scan converted data (data outputted from the scan converter 140), these embodiments can be implemented with data outputted from the beam former 120. Advantageously, this data has more information content than the scan converted data. Reprocessing can enhance specific features in the data by removing some of the constraints inherent in ultrasound imaging systems. Data can be processed and scan converted for alternate display size or resolution. Data can be processed in ways not possible on the ultrasound system's hardware or not available on the specific system. Removing the real-time imaging constraint opens the data to processing algorithms. Phase aberration correction or adaptive beamforming technologies not consistent with real-time processing of compatible with the system hardware can be applied to element data to improve image quality or enhance specific features. Strain (elasticity) algorithms can be performed on RF data to provide information on the texture of the tissue not available in the original image. Phase information available in the I/Q data can be used to reduce artifacts in line interpolation between receive lines.

Finally, as mentioned above, the ultrasound system can transfer saved ultrasound data to the workstation 300. In prior systems, the data transferred to the workstation was the exact data saved by a user at the ultrasound system. With these preferred embodiments, the "extra" stored data can also be sent to the workstation 300. In this way, the user at the workstation 300 can display a modification to the data requested to be stored at the ultrasound system 100. For example, a user at the ultrasound system 100 can position a region of interest indicator in one location, send the image to the workstation 300, and a user at the workstation 300 can reposition the region of interest indicator in another location.

It is intended that the foregoing detailed description be understood as an illustration of selected forms that the invention can take and not as a definition of the invention. It is only the following claims, including all equivalents, that are intended to define the scope of this invention.

What is claimed is:

1. A method for displaying a portion of an ultrasound image, the method comprising:
   (a) during image acquisition, positioning a region of interest indictor over a first portion of an ultrasound image;
   (b) storing the first portion and at least some other portion of the ultrasound image in a post-scan-converted format;
   (c) playing the stored ultrasound image;
   (d) positioning a region of interest indicator over a second portion of the played ultrasound image; and
   (e) playing the second portion.

2. The method of claim 1, wherein the first portion and the at least some other portion of the ultrasound image comprise a full-frame ultrasound image.

3. The method of claim 1 further comprising, between (b) and (c), playing the first portion.

4. The method of claim 3, wherein the first portion is played in one quadrant of a four-quadrant display.

5. The method of claim 1, wherein the stored ultrasound image comprises a plurality of frames, and wherein (c) comprises displaying only a single frame of the plurality of frames.

6. The method of claim 1, wherein the stored ultrasound image comprises a plurality of frames, and wherein (c) comprises playing at least two of the plurality of frames.

7. The method of claim 1, wherein the second portion is played in one quadrant of a four-quadrant display.

8. The method of claim 1, wherein the second portion is ¼ the size of a full-frame ultrasound image.

9. The method of claim 1, wherein (a)–(e) are performed by a medical diagnostic ultrasound imaging system.

10. The method of claim 1, wherein (a)–(b) are performed by a medical diagnostic ultrasound imaging system, and wherein (c)–(e) are performed by a workstation.

11. The method of claim 10 further comprising:
    making the stored ultrasound image DICOM compliant; and then
    transferring the stored ultrasound image from the medical diagnostic ultrasound imaging system to the workstation.

12. The method of claim 10, wherein the stored ultrasound image is transferred to the workstation via a removable media device.

13. The method of claim 10, wherein the stored ultrasound image is transferred to the workstation via a network.

14. The method of claim 1, wherein the region of interest indictor in (a) is different from the region of interest indicator in (d).

15. The method of claim 1, wherein the region of interest indictor in (a) is the same as the region of interest indicator in (d), whereby (d) comprises repositioning the region of interest indicator from the first portion to the second portion.

16. The method of claim 1, wherein the first portion and the at least some other portion of the ultrasound image are stored in a standard pixel data format.

17. A method for displaying a portion of an ultrasound image, the method comprising:
    (a) storing an ultrasound image in a post-scan-converted format;
    (b) playing the ultrasound image;
    (c) positioning a region of interest indicator over a portion of the ultrasound image;
    (d) playing the portion of the ultrasound image;
    (e) positioning a region of interest indicator over a second portion of the ultrasound image; and
    (f) playing the second portion of the ultrasound image.

18. The method of claim 17, wherein the ultrasound image comprises a plurality of frames, and wherein (b) comprises displaying only a single frame of the plurality of frames.

19. The method of claim 17, wherein the ultrasound image comprises a plurality of frames, and wherein (b) comprises playing at least two of the plurality of frames.

20. The method of claim 17, wherein the portion of the ultrasound image is played in one quadrant of a four-quadrant display.

21. The method of claim 17, wherein the portion is ¼ the size of the ultrasound image.

22. The method of claim 17, wherein (a)–(d) are performed by a medical diagnostic ultrasound imaging system.

23. The method of claim 17, wherein (a) is performed by a medical diagnostic ultrasound imaging system, and wherein (b)–(d) are performed by a workstation.

24. The method of claim 23 further comprising:
    making the ultrasound image DICOM compliant; and then
    transferring the stored ultrasound image from the medical diagnostic ultrasound imaging system to the workstation.

25. The method of claim 23, wherein the stored ultrasound image is transferred to the workstation via a removable media device.

26. The method of claim 23, wherein the stored ultrasound image is transferred to the workstation via a network.

27. The method of claim 17, wherein the ultrasound image is acquired during image acquisition, and wherein a region of interest indicator is not positioned over the ultrasound image during image acquisition.

28. The method of claim 17, wherein the ultrasound image stored in (a) comprises a full-frame ultrasound image.

29. The method of claim 17, wherein the ultrasound image is stored in a standard pixel data format.

30. The method of claim 17, wherein the region of interest indicator in (c) is the same as the region of interest indicator in (f).

31. The method of claim 17, wherein the region of interest indicator in (c) is different from the region of interest indicator in (f).

32. A system for displaying a portion of an ultrasound image, the system comprising:
- a medical diagnostic ultrasound imaging system operative to:
  - during image acquisition, position a region of interest indictor over a first portion of an ultrasound image; and
  - store the first portion and at least some other portion of the ultrasound image in a post-scan-converted format; and
- a workstation in communication with the medical diagnostic ultrasound imaging system, the workstation operative to:
  - receive the stored ultrasound image from the medical diagnostic ultrasound imaging system;
  - play the ultrasound image;
  - position a region of interest indicator over a second portion of the ultrasound image; and
  - play the second portion of the ultrasound image.

33. The system of claim 32, wherein the workstation is in communication with the medical diagnostic ultrasound imaging system via a network.

34. The system of claim 32, wherein the workstation is in communication with the medical diagnostic ultrasound imaging system via a removable media device.

35. The system of claim 32, wherein the medical diagnostic ultrasound imaging system is further operative to make the stored ultrasound image DICOM compliant before transferring it to the workstation.

36. The system of claim 32, wherein the first portion and the at least some other portion are stored in a standard pixel data format.

37. A method for displaying a portion of an ultrasound image, the method comprising:
- (a) receiving a request to store a multi-frame ultrasound image for a first length of time;
- (b) storing the multi-frame ultrasound image for a second length of time, the second length of time being longer than the first length of time;
- (c) receiving a request to play the multi-frame ultrasound image; and
- (d) playing the multi-frame ultrasound image.

38. The method of claim 37, wherein (c) comprises receiving a request to play the multi-frame ultrasound image for the first length of time.

39. The method of claim 37, wherein (c) comprises receiving a request to play the multi-frame ultrasound image for a length of time less than the first length of time.

40. The method of claim 37, wherein (c) comprises receiving a request to play the multi-frame ultrasound image for a length of time greater than the first length of time but less than the second length of time.

41. The method of claim 37, wherein (c) comprises receiving a request to play the multi-frame ultrasound image for the second length of time.

42. The method of claim 37, wherein the first length of time comprises a systole portion of a heart cycle, and wherein the second length of time comprises a full heart cycle.

43. The method of claim 37 further comprising displaying a visual indicator indicating a length of the multi-frame ultrasound image to be played as compared to the second length of time.

44. The method of claim 43, wherein the visual indicator comprises movable first and second portions allowing the user to adjust starting and stopping points of the playback of the stored multi-frame ultrasound image.

45. The method of claim 37, wherein the multi-frame ultrasound image is stored in a post-scan-converted format.

46. The method of claim 37, wherein the multi-frame ultrasound image is stored in a pre-scan-converted format.

47. The method of claim 37, wherein the multi-frame ultrasound image is stored in a pre-detected, RF data format.

48. The method of claim 37, wherein (a)–(b) are performed by a medical diagnostic ultrasound imaging system, and wherein (c)–(d) are performed by a workstation.

49. A method for displaying ultrasound data, the method comprising:
- (a) receiving a request to store one or more ultrasound images;
- (b) storing more data than is necessary for a redisplay of the requested one or more ultrasound images, the data being selected from the group consisting of element data, beamformed data, I/Q data, and scan converted data;
- (c) receiving a request to display at least some of the stored data; and
- (d) displaying the requested data.

50. The method of claim 49, wherein (b) comprises storing enough data to redisplay the one or more ultrasound images.

51. The method of claim 49, wherein the data stored in (b) comprises more spatial data than is necessary for a redisplay of the requested one or more ultrasound images.

52. The method of claim 49, wherein the data stored in (b) comprises more temporal data than is necessary for a redisplay of the requested one or more ultrasound images.

53. The method of claim 49, wherein the data stored in (b) requires additional processing to be display in (d).

54. The method of claim 49, wherein (a)–(b) are performed by a medical diagnostic ultrasound imaging system, and wherein (c)–(d) are performed by a workstation.

55. A method for displaying a portion of an ultrasound image, the method comprising:
- (a) storing an ultrasound image in a post-scan-converted format;
- (b) playing the ultrasound image;
- (c) positioning a region of interest indicator over a portion of the ultrasound image; and
- (d) playing the portion of the ultrasound image;
- wherein (a) is performed by a medical diagnostic ultrasound imaging system, and wherein (b)–(d) are performed by a workstation separate from the medical diagnostic ultrasound imaging system.

56. The method of claim 55, wherein the ultrasound image comprises a plurality of frames, and wherein (b) comprises displaying only a single frame of the plurality of frames.

57. The method of claim 55, wherein the ultrasound image comprises a plurality of frames, and wherein (b) comprises playing at least two of the plurality of frames.

58. The method of claim 55, wherein the portion of the ultrasound image is played in one quadrant of a four-quadrant display.

59. The method of claim 55, wherein the portion is ¼ the size of the ultrasound image.

60. The method of claim 55 further comprising:
- making the ultrasound image DICOM compliant; and then
- transferring the stored ultrasound image from the medical diagnostic ultrasound imaging system to the workstation.

61. The method of claim 55, wherein the stored ultrasound image is transferred to the workstation via a removable media device.

62. The method of claim 55, wherein the stored ultrasound image is transferred to the workstation via a network.

63. The method of claim 55, wherein the ultrasound image is acquired during image acquisition, and wherein a region of interest indicator is not positioned over the ultrasound image during image acquisition.

64. The method of claim 55, wherein the ultrasound image stored in (a) comprises a full-frame ultrasound image.

65. The method of claim 55, wherein the ultrasound image is stored in a standard pixel data format.

* * * * *